United States Patent [19]

Abrams et al.

[11] Patent Number: 4,769,489

[45] Date of Patent: Sep. 6, 1988

[54] CATALYST RECOVERY METHOD

[75] Inventors: Kenneth J. Abrams, Naperville; Daniel W. Marsh, Lisle; Bruce B. Doll, Downers Grove, all of Ill.

[73] Assignee: Amoco Corporation, Chicago, Ill.

[21] Appl. No.: 890,129

[22] Filed: Jul. 28, 1986

[51] Int. Cl.[4] ............................................ C07C 51/265
[52] U.S. Cl. .................................... 562/416; 562/414
[58] Field of Search .............................. 562/414, 416

Primary Examiner—Michael L. Shippen
Attorney, Agent, or Firm—James R. Henes; William H. Magidson; Ralph C. Medhurst

[57] ABSTRACT

A catalyst-recovery method for catalyst used in a continuous liquid-phase oxidation process of an aromatic alkyl to an aromatic carboxylic acid product is disclosed. The aromatic carboxylic acid product is withdrawn from an oxidation reactor as an aqueous product and is thereafter subjected to crystallization to produce the aromatic carboxylic acid product and a product mother liquor stream. The product mother liquor stream is separated into a solvent-rich stream and a solids-containing catalyst-rich stream. The solids-containing catalyst-rich stream is separated into a by-product cake and a catalyst-bearing stream that is substantially free from solids. A portion of the catalyst-bearing stream is contacted with the vapor stream passing through the absorber system, and a catalyst-rich bottoms stream is thereafter withdrawn from the absorber system. A portion of the catalyst-rich bottoms stream is returned to the reactor.

4 Claims, 1 Drawing Sheet

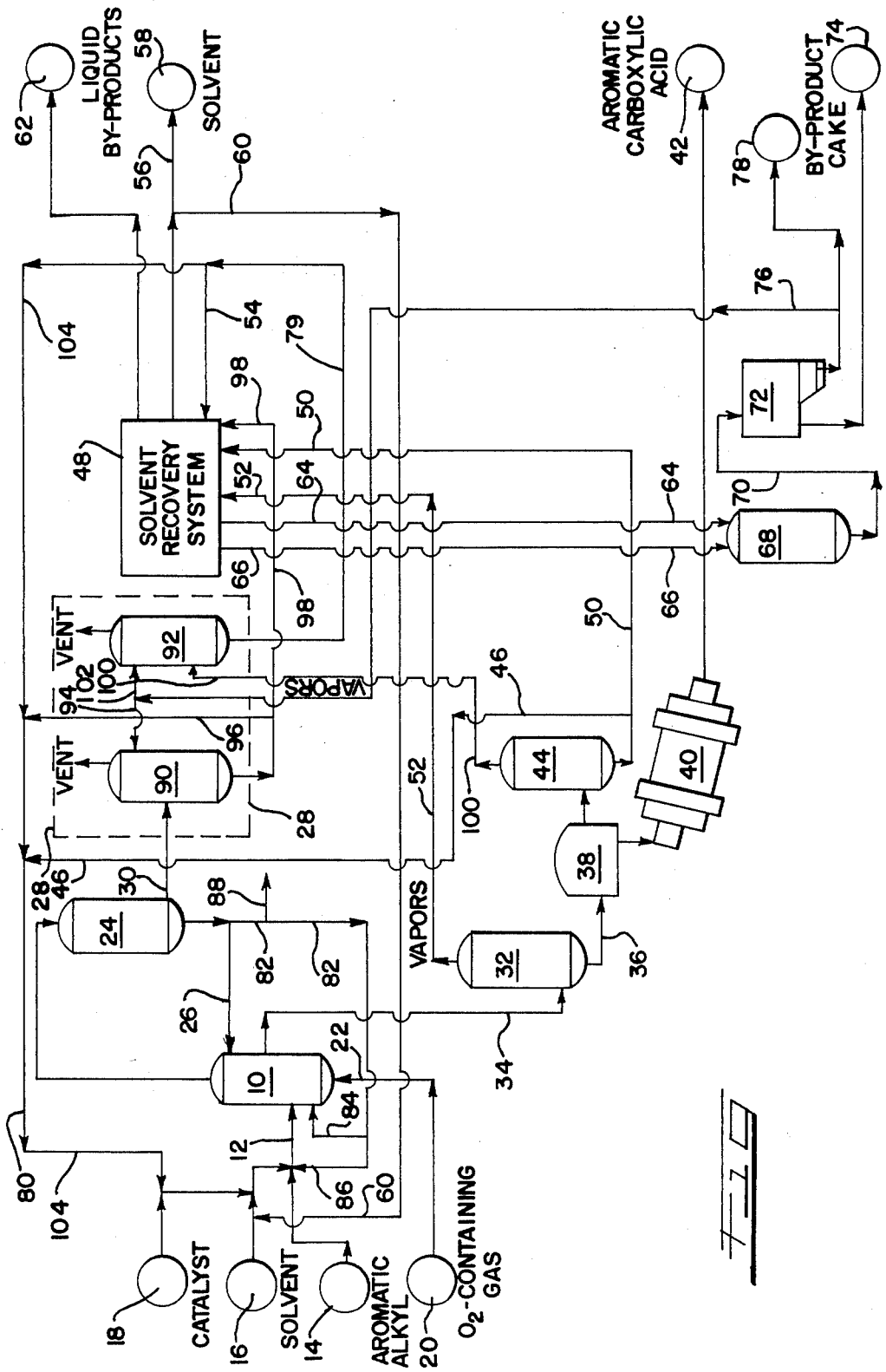

CATALYST RECOVERY METHOD

TECHNICAL FIELD OF THE INVENTION

This invention relates generally to the catalytic oxidation of an aromatic alkyl to an aromatic carboxylic acid. The present invention, in particular, is directed to a method for recovering the oxidation catalyst.

BACKGROUND OF THE INVENTION

Aromatic alkyls are commonly catalytically oxidized to aromatic carboxylic acids, in the liquid phase, within a pressurized oxidation reactor. Such liquid-phase reaction systems are shown in U.S. Pat. Nos. 3,170,768 and 3,092,658, both to Baldwin. The reaction medium contained within the reactor typically includes the aromatic alkyl, a volatilizable aqueous solvent, an oxygen-containing gas, and the oxidation catalyst.

The oxidation reaction is exothermic. A substantial portion of the reaction-generated heat is removed by evaporating a portion of the reaction mixture from the reactor, withdrawing this portion from the reactor as a reactor overhead vapor stream, partially condensing this vapor stream and returning the condensate to the reactor. The remainder of the vapor stream is conventionally passed through an absorber system to recover unreacted aromatic alkyl and solvent.

A product stream, containing the aromatic carboxylic acid product solvent, oxidation reaction by-products and catalyst, is withdrawn from the reactor and is passed through crystallizers. A typical product stream contains about 1-6 parts by weight of a liquid phase containing about 15 weight percent of water and about 85 weight percent solvent, typically acetic acid, and about one part by weight of the aromatic carboxylic acid product. The crystallizers concentrate the aqueous product stream by removing a portion of the water, solvent, and volatilizable by-products. The thus-concentrated product stream, exiting the crystallizers and bearing crystals of product, contains the remainder of the solvent, the remainder of the reaction by-products, and the catalyst. These by-products together with the catalyst are commonly referred to as oxidation residue. The concentrated product stream is separated into aromatic carboxylic acid product crystals and an aqueous aromatic carboxylic acid product mother liquor stream.

Conventionally, at least a portion of the product mother liquor stream is passed through a solvent recovery system to separate the residue from the solvent. The residue is typically combined with an extraneous water stream to produce an extraction slurry. The extraction slurry is then separated into so-called waste solids and a catalyst-containing mother liquor, which is thereafter concentrated in an evaporation step. Finally, the concentrated catalyst-containing mother liquor is recycled to the reactor.

The conventional catalyst-concentrating step is typically achieved via an evaporative system that entails substantial capital investment. The variable costs of the evaporation system, moreover, include steam, cooling water, and electrical costs. The evaporation system equipment includes evaporator reboilers, condensers, separators, and a variety of pumps and agitated vessels. There are also maintenance expenses associated with this equipment.

The present invention is a catalyst-recovery method which results in significantly lower capital and variable costs in the overall oxidation process as compared to conventional processes. In particular, the present catalyst-recovery method renders unnecessary substantially all of the above-enumerated catalyst-recovery evaporation system equipment, and its associated maintenance and operating expenses that are typically required in connection with conventional processes.

SUMMARY OF THE INVENTION

Briefly, the present catalyst-recovery method contemplates separating an aqueous product mother liquor stream from an oxidation reactor into a solvent-rich stream and a solids-containing catalyst rich stream. A catalyst-bearing stream that is substantially free from solids is recovered from the catalyst-rich stream and a portion thereof is thereafter contacted in an absorber system with the reactor overhead vapor stream that is passing through the absorber system. A catalyst-rich bottoms stream is withdrawn from the absorber system, and at least a portion of this bottoms stream is returned to the reactor for reuse.

BRIEF DESCRIPTION OF THE FIGURE

The accompanying FIGURE is a process flow diagram illustrating a system embodying the principles of the catalyst-recovery method of the present invention.

DETAILED DESCRIPTION OF ILLUSTRATED EMBODIMENT

While the present invention is susceptible to embodiment in various forms, there is shown in the accompanying FIGURE, and hereinafter described in detail, a preferred embodiment of the invention. The present disclosure is to be considered as an exemplification of the invention without limitation to the specific embodiment illustrated, however.

Referring to the accompanying FIGURE, a reactor feed mixture is introduced into oxidation reactor 10 via conduit 12. The reactor feed mixture comprises an aromatic alkyl from source 14, a volatilizable, aqueous aliphatic acid solvent from source 16, and an oxidation catalyst from source 18. The feed mixture may further include a suitable promoter. An oxygen-containing gas from source 20 is separately introduced into reactor 10 via conduit 22. The preferred oxygen-containing gas is air. The volatilizable solvent employed is typically an aqueous monocarboxylic $C_2$ to $C_6$ aliphatic acid.

Reactor 10 is a pressurized, vented oxidation reactor vessel wherein liquid-phase exothermic oxidation of the aromatic alkyl by the oxygen-containing gas takes place in the presence of the oxidation catalyst. The reaction medium contained by reactor 10 thus comprises the oxygen-containing gas, the aromatic alkyl that is to be oxidized to an aromatic carboxylic acid product, the oxidation catalyst, and the aliphatic acid solvent. During the course of the reaction, oxidation reaction by-products are also produced. The reactants in reactor 10 are maintained at an elevated pressure sufficient to maintain the contained, volatilizable reaction medium substantially in the liquid state at the reaction temperature.

During the course of the oxidation reaction, at least a portion of the exothermic heat of reaction is removed from reactor 10 by vaporization of a portion of the reaction medium to produce a reactor overhead vapor stream. A portion of the reactor overhead vapor stream is condensed in a condenser system 24 and at least a portion of the condensate is refluxed to reactor 10 via conduit 26. The remainder of the reactor overhead vapor stream that is not condensed in the condenser system 24 is passed to an absorber system 28 via conduit 30 for recovery of unreacted aromatic alkyl and solvent.

The product stream, containing the aromatic carboxylic acid, is withdrawn from reactor 10 and is introduced into a crystallization system 32 via conduit 34. Within crystallization system 32, the aqueous product stream is concentrated into a product crystal-bearing slurry stream, volatile components of the aqueous product stream being removed from the crystal-bearing slurry stream by the crystallization system 32. From crystallization system 32, the product crystal-bearing slurry stream is conveyed via conduit 36 to a separator such as vacuum filter 38. In operation, vacuum filter 38 recovers aromatic carboxylic acid crystals and produces an aromatic carboxylic acid mother liquor stream which contains the oxidation reaction by-products and catalyst. The aromatic carboxylic acid crystals from vacuum filter 38 are dried in a dryer 40 and thereafter passed to a suitable site or facilities 42 for storage or further processing as desired.

The aromatic carboxylic acid mother liquor being withdrawn from vacuum filter 38 is received by vessel 44 which is adapted to collect and separate volatile components from the non-volatile components of the aromatic carboxylic acid mother liquor and to pass a portion of the non-volatilized product mother liquor via conduit 46 back to the reactor 10 for direct recovery of a portion of the aromatic carboxylic acid product and a portion of the catalyst. The remainder of the non-volatilized product mother liquor from vessel 44 is passed to a solvent recovery system 48 via conduit 50 to recover the solvent.

Briefly, solvent recovery system 48 is also supplied aqueous solvent-rich vapors from the crystallization system 32 via conduit 52, and is further supplied with an aqueous solvent-containing stream from absorber system 28 via conduits 54 and 79. In operation, solvent recovery system 48 produces a liquid by-product stream, a catalyst-rich solid by-product stream, an aqueous process stream, and a recovered-solvent stream.

Recovered solvent from solvent recovery system 48 can be passed via conduit 56 to a suitable site or facilities 58 for storage, or further processing as desired, or can be recycled to reactor 10 via conduit 60. The liquid by-product stream from solvent recovery system 48 can be passed to a suitable site or facilities 62 for storage, further processing or disposal, as desired.

The aqueous process stream and the catalyst-rich solid by-product stream are separately conveyed from solvent recovery system 48 by conduits 64 and 66, respectively, to mixing vessel 68 which can include an agitator (not shown). An aqueous by-product-containing and catalyst-rich mixture is withdrawn from mixing vessel 68 and is conveyed via conduit 70 into a separator such as centrifuge 72. Centrifuge 72 separates this aqueous mixture into a by-product cake and a catalyst-bearing stream that is substantially free from by-product solids. The by-product cake can be passed from centrifuge 72 to a suitable site or facilities 74 for storage, further processing or disposal, as desired.

In accordance with the principles of the present invention, a portion or all of the catalyst-bearing stream from centrifuge 72 is passed through absorber system 28 via conduit 76. That is, at times it may be desirable to bleed some of the catalyst-bearing stream from the aromatic carboxylic acid-producing system shown in the accompanying FIGURE and to convey such a bleed stream to a suitable site or facilities 78 to remove a particular stream component from the system, or for start-up, shut-down or other purposes. Generally, however, the catalyst-bearing stream from centrifuge 72 is passed to the absorber system 28 in the manner and for the purpose described above, and is thereafter withdrawn from absorber system 28 as a catalyst-rich bottoms stream 79. This catalyst-rich bottoms stream is returned to reactor 10 via conduits 80 and 104.

The catalyst-recovery method of the present invention can, moreover, be used to recover catalyst in a number of conventional systems or processes that currently produce a variety of aromatic carboxylic acid products. For example, aromatic alkyls that are suitable as reactor feed-mixture components or ingredients in accordance with the principles of the present invention include toluene, o-xylene, m-xylene, p-xylene and the trimethylbenzenes. The respective aromatic carboxylic acid products of these aromatic alkyls are benzoic acid, orthophthalic acid, isophthalic acid, terephthalic acid (TPA), and the benzenetricarboxylic acids. The method of this invention is thus well suited to produce TPA, isophthalic acid, and trimellitic acid (1,2,4-benzenetricarboxylic acids). It is particularly well-suited for the production of TPA.

Suitable aqueous aliphatic acid solvents useful in the method of this invention are those that are readily volatilizable at the specific reaction temperature employed. Among such solvents are aqueous solutions of $C_2$ to $C_6$ monocarboxylic acids, e.g., acetic acid, propionic acid, n-butyric acid, isobutyric acid, n-valeric acid, trimethylacetic acid, caproic acid, and mixtures thereof. When this invention is used in connection with the production of TPA, the preferred volatilizable monocarboxylic aliphatic acid solvent is aqueous acetic acid.

The method of the present invention is useful for recovery of a variety of oxidation reaction catalyst. For example, in connection with the catalytic oxidation of an aromatic alkyl to an aromatic carboxylic acid, typical catalysts and/or catalyst systems include mixtures of cobalt, manganese and bromine compounds or complexes, soluble in the particular volatilizable aqueous solvent employed. When the aromatic carboxylic acid-producing system shown in the accompanying FIGURE is used to produce TPA, a preferred catalyst system is a solution prepared from dry cobalt, selected manganese acetates and water. Such preferred catalyst system includes aqueous hydrogen bromide as a promoter.

In connection with the production of TPA, the remainder of the aromatic carboxylic acid-producing system shown in the accompanying FIGURE will now be discussed. As mentioned above, a portion of the reactor overhead vapor stream that is condensed in condenser system 24 is refluxed to reactor 10 via conduit 26. The remainder of the condensate is returned via conduit 82 to reactor 10. It may be desirable to return this condensate directly into reactor 10 via direct-return pipeline 84 or, from time to time, it may be desirable to return this condensate upstream of reactor 10 as indirect recycle via conduit 86. It may also be desirable to withdraw a portion of the condensate from conduit 82 as a trim stream via conduit 88, for a variety of reasons.

In connection with the production of TPA, the absorber system 28 includes a vented, high-pressure absorber 90 that is pressurized to about 12 kilograms per square-centimeter gauge (about 171 pounds per square-inch gauge), and a vented, atmospheric absorber 92. Those above-mentioned reactor overhead vapors which are not condensed in condenser system 24, and are passed to absorber system 28 via conduit 30, are received by high-pressure absorber 90. The air rate from source 20 to reactor 10 is preferably adjusted so that the vent-gas oxygen concentration of high-pressure absorber 90 ranges from about 1 to about 3 volume percent oxygen on a volatile-free basis. Also as mentioned above, a portion of the catalyst-bearing stream from centrifuge 72 is passed through absorber system 28 via conduit 76.

In particular, a portion of that catalyst-bearing stream from conduit 76 is introduced into high-pressure absorber 90 via conduit 94 to scrub the vapors being conveyed into high-pressure absorber 90 via conduit 30 to recover unreacted aromatic alkyl. In general, the catalyst-rich bottoms stream from high-pressure absorber 90 is returned to reactor 10 via conduit 96, although a portion of the high-pressure absorber bottoms stream can be passed to the solvent recovery system 48 via conduit 98 to recover solvent, or for start-up and/or shut-down purposes, as desired. Further, as mentioned above, absorber system 28 receives solvent-rich vapors from vessel 44 for solvent-recovery purposes. In particular, such vapors are introduced into atmospheric absorber 92 via conduit 100 to scrub these solvent-rich vapors to recover the solvent.

The remainder of the catalyst-bearing stream from conduit 76 is introduced into atmospheric absorber 92 via conduit 102 to recover solvent, with the solvent-rich vapors being conveyed into the atmospheric absorber 92 via conduit 100. A catalyst-rich and solvent-containing bottoms stream 79 is withdrawn from atmospheric absorber 92. A portion of bottoms stream 79 is passed to solvent recovery system 48 via conduit 54 to recover solvent, as mentioned above, while the remainder of this bottoms stream 79 is returned to reactor 10 via conduits 80 and 104 to reuse the catalyst. Preferably, in the production of TPA, at least about 80 weight percent of the atmospheric absorber bottoms from bottoms stream 79 are returned to reactor 10 via conduit 104.

What has been illustrated and described herein is a new catalyst-recovery method. While the catalyst-recovery method of the present invention has been illustrated and described with reference to a presently preferred system embodied in the accompanying FIGURE, the present invention is not limited thereto. That is, the present invention generally relates to catalyst recovery in connection with a wide variety of aromatic carboxylic acid products which are or can be continuously produced by the liquid-phase, exothermic, catalytic oxidation of an aromatic alkyl with an oxygen-containing gas. For example, the catalyst-recovery method of the present invention in addition to the above-mentioned aromatic alkyls is also generally applicable, as an example of the scope of the present invention, to the catalytic oxidation of each of the below-listed aromatic alkyls to its respective aromatic carboxylic acid product:

methylbenzene: benzoic acid
1,2,3,4-tetramethylbenzene: prehnitic acid
1,2,3,5-tetramethylbenzene: mellophanic acid
1,2,4,5-tetramethylbenzene: pyromellitic acid
pentamethylbenzene: benzenepenta-carboxylic acid
hexamethylbenzene: mellitic acid
1,3-dimethyl-5-ethylbenene: trimesic acid
1-methylnaphthalene: $\alpha$-naphthoic acid
2-methylnaphthalene: $\beta$-naphthoic acid
3-methylpyridine: nicotinic acid Thus, alternatives, changes or modifications may become apparent to those skilled in the art upon reading the foregoing description. Accordingly, such alternatives, changes and modifications are to be considered as forming a part of the invention insofar as they fall within the spirit and scope of the appended claims.

We claim:

1. In a method for the continuous production of an aromatic carboxylic acid product by liquid-phase, exothermic oxidation of an aromatic alkyl with an oxygen-containing gas in the presence of an oxidation catalyst comprising cobalt, manganese, and bromine components and in an aqueous solvent medium present in an oxidation reactor, wherein heat generated in the oxidation reaction is dissipated at least in part by refluxing a portion of a reactor overhead vapor stream, with the remainder of the vapor stream being passed on to an absorber system for recovery of unreacted aromatic alkyl and solvent, and wherein product stream is withdrawn from the reactor and thereafter subjected to crystallization to produce a solid product stream and a mother liquid stream, the improvement which comprises:
separating the mother liquor stream into a solvent-rich stream and a solids-containing catalyst-rich stream;
recovering a catalyst-bearing stream that is substantially free from solids from said catalyst-rich stream;
contacting at least a portion of the recovered catalyst-bearing stream with a vapor stream portion passing through the absorber system;
withdrawing from the absorber system a catalyst-rich bottoms stream; and
recycling at least a portion of the bottoms stream to the reactor.

2. The method in accordance with claim 1 wherein the catalyst-bearing stream is recovered by separating solids from the solids-containing catalyst-rich stream in the form of a by-product cake.

3. The method in accordance with claim 1 wherein the solvent-rich stream is passed through the absorber system to recover solvent.

4. The method in accordance with claim 3 further including the step of passing the remainder of the absorber system bottoms stream to a solvent recovery system to recover solvent from the bottoms stream.

* * * * *